United States Patent
Jurek et al.

(10) Patent No.: US 11,078,336 B2
(45) Date of Patent: Aug. 3, 2021

(54) ALKOXYLATED DISPERSING AGENTS

(71) Applicant: SUN CHEMICAL CORPORATION, Parsippany, NJ (US)

(72) Inventors: Michael J. Jurek, Oak Ridge, NJ (US); Juanita Parris, Montvale, NJ (US)

(73) Assignee: Sun Chemical Corporation, Parsippany, NJ (US)

( * ) Notice: Subject to any disclaimer, the term of this patent is extended or adjusted under 35 U.S.C. 154(b) by 319 days.

(21) Appl. No.: 15/772,695

(22) PCT Filed: Nov. 9, 2016

(86) PCT No.: PCT/US2016/061034
§ 371 (c)(1),
(2) Date: May 1, 2018

(87) PCT Pub. No.: WO2017/083321
PCT Pub. Date: May 18, 2017

(65) Prior Publication Data
US 2019/0322813 A1    Oct. 24, 2019

Related U.S. Application Data

(60) Provisional application No. 62/253,279, filed on Nov. 10, 2015, provisional application No. 62/256,290, filed on Nov. 17, 2015.

(51) Int. Cl.
| | |
|---|---|
| *C08G 81/02* | (2006.01) |
| *C08G 18/28* | (2006.01) |
| *C08G 63/91* | (2006.01) |
| *C08K 3/22* | (2006.01) |
| *C08K 5/12* | (2006.01) |
| *C08L 67/02* | (2006.01) |
| *C08L 71/02* | (2006.01) |
| *C09D 11/101* | (2014.01) |
| *C09D 11/104* | (2014.01) |
| *C09D 11/107* | (2014.01) |
| *C09D 11/326* | (2014.01) |

(52) U.S. Cl.
CPC ......... *C08G 81/024* (2013.01); *C08G 18/283* (2013.01); *C08G 63/916* (2013.01); *C08K 3/22* (2013.01); *C08K 5/12* (2013.01); *C08L 67/025* (2013.01); *C08L 71/02* (2013.01); *C09D 11/101* (2013.01); *C09D 11/104* (2013.01); *C09D 11/107* (2013.01); *C09D 11/326* (2013.01)

(58) Field of Classification Search
CPC ...... C08G 18/283; C08G 63/916; C08K 3/22; C08K 5/12; C08L 67/025; C08L 71/02
USPC .......................................................... 523/160
See application file for complete search history.

(56) References Cited

U.S. PATENT DOCUMENTS

| | | |
|---|---|---|
| 3,781,379 A | 12/1973 | Theodore et al. |
| 5,684,081 A | 11/1997 | Dannhorn et al. |
| 5,852,118 A | 12/1998 | Horrion et al. |
| 6,435,873 B1 | 8/2002 | Burgio |
| 8,357,759 B2 * | 1/2013 | Montiel ............... C08F 269/00 525/299 |
| 2004/0082680 A1 * | 4/2004 | Phelan .................. G02B 1/043 522/90 |
| 2005/0255330 A1 | 11/2005 | Meyer |
| 2011/0133122 A1 * | 6/2011 | Lista .................. C08G 18/4252 252/182.12 |
| 2012/0128874 A1 | 5/2012 | Okoniewski |
| 2014/0037711 A1 * | 2/2014 | Parakka ................. A61L 15/64 424/444 |
| 2014/0271607 A1 | 9/2014 | Kim et al. |

OTHER PUBLICATIONS

Extended European Search Report issued in counterpart EP Application No. 16846876.4, dated Apr. 24, 2019.
International Preliminary Report issued in PCT/US2016/061034, dated May 15, 2018.
International Search Report issued in International Application No. PCT/US2016/061034, dated Feb. 15, 2017.
Written Opinion of the International Searching Authority issued in International Application No. PCT/US2016/061034, dated Feb. 15, 2017.
Mahoney, MJ et al., "Three-dimensional growth and function of neural tissue in degradable polyethylene glycol hydrogels. Biomaterials," vol. 27, 2006, pp. 2265-2274.

* cited by examiner

*Primary Examiner* — Doris L Lee
(74) *Attorney, Agent, or Firm* — Marian E. Fundytus; Ostrolenk Faber LLP.

(57) ABSTRACT

Described herein are alkoxylated polymers suitable for use in primers, inks or coating compositions. The alkoxylated polymers derive from a polyalkylene glycol polymer or copolymer backbone having one or more alkoxylated sites in a non-reactive form and at least one reactive terminal end, and one or more polyfunctional monomers or oligomers having two or more functional polar groups with an active hydrogen, or mixtures thereof, wherein the alkoxylated polymer is polymerized in a one step process. Primers, inks or coating compositions are further described.

31 Claims, No Drawings

ALKOXYLATED DISPERSING AGENTS

The present application is a § 371 National Phase application based on PCT/US2016/061034 filed Nov. 9, 2016, which claims the benefit of U.S. Provisional Application Nos. 62/256,290, filed Nov. 17, 2015, and 62/253,279, filed Nov. 10, 2015 the subject matter of each of which is incorporated by reference in their entirety.

BACKGROUND

Many printers seek to increase their productivity by employing high speed printing. However, as printing speed increases, there is a greater tendency for printing defects to occur. Moreover, because of the constraints placed upon ink formulations suitable for high speed printing, other properties, such as opacity, gloss, scratch resistance, and laydown of the ink may be compromised.

Because high speed printing inks and coatings may have a low viscosity, the amount of solids in a formulation should be reduced. However, when reducing the amount of solids in an ink or coating, it becomes a challenge to load enough colorant in order to attain the desired opacity and gloss. Thus, there may be a compromise between the opacity and gloss of the ink and the printing speed.

Gloss is affected by the smoothness of a printed ink or coating. Rough coatings reflect less light, and thus gloss will be reduced. Therefore, it is important that the laydown of an ink or coating be sufficient to form a smooth printed surface.

Other ink or coating durability properties, such as scratch resistance, are also affected in inks formulated for high speed printing. Low viscosity inks containing binders and resins suitable for printing at high speed often produce tacky, soft print surfaces which are not durable. Other properties such as scratch resistance are also compromised.

The seemingly incompatible characteristics sought for a high speed printing ink or coating present challenges to the ink formulator. While a high speed printing ink or coating should be of a low viscosity, reducing the solids content to achieve low viscosity may adversely affect opacity. Thus, to achieve a high opacity ink, the ink should include a higher solids loading (e.g., colorant), which leads to higher viscosity. Also, while durable inks and coatings are desired, binders and resins that have a low viscosity suitable for high speed printing are often not durable.

Coating and ink compositions (such as primers, varnishes, paints, coatings, and printing inks) may be colored by the incorporation of dyes or pigments. While dyes are generally soluble, pigments are not. Therefore, to achieve good color intensity, gloss, hiding power, lightfastness, weather resistance etc. when pigments are used, the pigment particles should be homogeneously mixed into the composition.

Pigments are dispersed in the liquid ink or coating composition to provide a homogeneous mixture. Stable pigment dispersions may be formed by (1) wetting the pigment particles (or aggregates or agglomerates of pigment particles) with the coating solution (e.g., resin solution); (2) dispersing the pigment particles in the liquid by applying mechanical energy; and (3) stabilizing the dispersion. Dispersing agents can be used to achieve the first and third steps.

During wetting, the resin solution displaces the air between the pigment particles, aggregates, and/or agglomerates. To aid the wetting of the pigment particles, a dispersing agent (also known as a surfactant) may be added to the composition to modify the surface tension of the liquid and the interfacial tension between the liquid and the pigment particles.

During the second (dispersing) step, mechanical force, in the form of impact and shear forces, is applied to the ink and coating composition, such as applying forces to the composition with a bead mill or a roll mill to break up the pigment agglomerates into smaller units. This would lead to uniform distribution and dispersion in the liquid composition. With the third step of stabilization, the pigment particles are prevented from regrouping or flocculating. Without stabilization, the pigment may no longer be dispersed. The presence of dispersing agents in the liquid composition stabilizes the pigment particles, and prevents them from flocculating.

Polymeric dispersants are one kind of dispersing agents. Polymeric dispersants stabilize the dispersion by "steric stabilization". One part of a polymeric dispersant, the anchoring group, adsorbs onto the pigment particles. The other part, the polymeric chain, is soluble in the liquid composition, and thus extends into the liquid composition. A layer is formed around the pigment particles, effectively keeping them separated, thereby preventing flocculation. The pigment particles thus remain evenly dispersed in the liquid composition.

WO 2010/149962 teaches the use of a styrenic branched addition copolymer as a dispersant in a gaseous, liquid or solid formulation, wherein the copolymer is obtainable by addition polymerization. These copolymers can be used as dispersants for pigments, inks, paints sealants, tinters, powder coatings, and injection molding applications.

US 2010/0145001 relates to a branched, hybrid polymer obtained by addition polymerization, preferably a free radical polymerization process, comprising organic chains and inorganic chains. The copolymers may be incorporated into compositions containing only a carrier or diluent, or also comprising an active ingredient. The copolymers are particularly suitable for use in laundry compositions, especially as agents to prevent transfer of dye back onto the fabric.

US 2011/0283908 is directed to high opacity polyurethane resins produced by the polymerization of polyisocyanates with polymeric polyols and subsequent chain extension with polyamines. The resins are capable of providing high opacity printing inks when formulated with white pigments.

Li, et. al., *Biodegradable Hyperbranched Amphiphilic Polyurethane Multiblock Copolymers Consisting of Poly (propylene glycol), Poly(ethylene glycol), and Polycaprolactone as in Situ Thermogels*, (Biomacromolecules, 2012, 13 (12), pp. 3977-3989) describes and compares certain biodegradable thermogels, that is hyperbranched polyurethane systems, and linear polyurethane systems comprised of polypropylene glycol and/or polyethylene glycol and polycaprolactone.

D. G. Barrett, *One-Step Syntheses of Photocurable Polyesters*, Macromolecules, vol. 43, issue 23, pp. 9660-9667, (2010) discloses several polymers, of which one was a polymer based on itaconic acid and polyethylene glycol as photocurable, insoluble systems for use in biomaterials.

Sahoo, et. al., *Influence of PEG Endgroup and Molecular Weight on Its Reactivity for Lipase-Catalyzed Polyester Synthesis*, Biomacromolecules, 7, 1042-1048 (2006) indicates that sebacic acid polyesters with polyethylene glycol could be made using physically immobilized lipase B from *Candida Antarctica* as the enzymatic polymerization catalyst.

Guelcher. et. al., *Synthesis of Biocompatible Segmented Polyurethanes from Aliphatic Diisocyanates and Diurea*

*Diol Chain Extenders*, Acta Biomaterialia 1 471-484 (2005), describes new medical-grade polyurethanes synthesized from less toxic aliphatic diisocyanates. In this work, biocompatible segmented polyurethane elastomers were synthesized from aliphatic diisocyanates (1,4-diisocyanato-butane (BDI) and lysine methyl ester diisocyanate (LDI)), novel diurea diol chain extenders based on tyrosine and tyramine, and a model poly(ethylene glycol) (PEG) diol soft segment. Both the PEG and polycaprolactone (PCL) diols demonstrated no toxic effects on human endothelial cells cultured in vitro and degraded to non-toxic decomposition products.

Thus, there remains a need for primers, inks or coating compositions that have high opacity and durability, while having a low viscosity suitable for high speed applications, such as high speed printing.

SUMMARY OF THE INVENTION

Described herein are alkoxylated polymers suitable for use as dispersing agents in primers, inks or coating compositions used in the printing industry. Also described herein are primers, inks, or coating compositions comprising the alkoxylated polymers. Such compositions exhibit reduced particle size in the resultant pigment dispersions, which leads to better laydown and improved opacity.

In a particular aspect, the alkoxylated polymers of the present application derive from components comprising a polyalkylene glycol polymer or copolymer backbone having one or more alkoxylated sites in a non-reactive form and at least one reactive terminal end; and one or more polyfunctional monomers or oligomers having two or more functional polar groups with an active hydrogen, or mixtures thereof.

In a preferred arrangement, the alkoxylated polymers described herein are polymerized in a one-step process, whereas previously polymerization was a two- or more-step process. The present polymerization process increases the efficiency of manufacture of these kinds of polymers.

In one aspect, polyalkylene glycol polymer or copolymer backbone having one or more alkoxylated sites in a non-reactive form and at least one reactive terminal end is selected from polyethylene glycol, polypropylene glycol, polybutylene glycol, and copolymers and terpolymers thereof, such as di- and tri-block copolymers and terpolymers thereof. These polymer materials provide at least one alkoxylated site in non-reactive form and at least one terminal end that is reactive, e.g., where further alkoxylation can occur by adding polyfunctional monomers or oligomers to the polymer. In a more particular aspect, polyalkylene glycol polymer or copolymer backbone is selected from polyethylene glycol, polypropylene glycol and copolymers thereof, e.g., di-block or tri-block copolymers of polyethylene glycol and polypropylene glycol.

In one aspect, the one or more polyfunctional monomers or oligomers have two or more functional polar groups independently selected from the group consisting of hydroxyl, carboxyl, anhydride, thiol, amino, imino or amido. In another aspect, at least one of the polyfunctional monomers and/or oligomers includes one or more functional hydroxyl groups. In another aspect, the polyfunctional monomer or oligomer is a diol, for example, diethylene glycol and neopentyl glycol. In yet another aspect, the diol further includes —COOH functionality, e.g., a COOH-functional diol such as dimethylolpropionic acid and dimethylolbutanoic acid.

In one particular aspect, the one or more polyfunctional monomers or oligomers are (a) one or more diols and/or polyols of functionality greater than that of a diol; and (b) one or more diacids or anhydrides, or mixtures thereof. The alkoxylated polymer resulting in this aspect may be an alkoxylated polyester.

In another particular aspect, the one or more polyfunctional monomers or oligomers are (a) one or more diols and/or polyols of functionality greater than that of a diol; and (b) one or more diisocyanates, or mixtures thereof. The alkoxylated polymer resulting in this aspect may be alkoxylated polyurethane. The alkoxylated polymer that is produced may also be an alkoxylated polyurethane-urea, with selection of the appropriate backbone and/or polyfunctional monomers or oligomers.

In one aspect, the alkoxylated polymers described herein are prepared by reacting a poly(alkylene glycol) with one terminal hydroxyl group with a diacid or anhydride to obtain a carboxyl functional reaction product, and reacting the carboxyl functional product with a hydroxyl functional base polymer at an equimolar ratio to form ester groups at each hydroxyl site on the base polymer. The poly(alkylene glycol) may be poly(ethylene glycol) poly(propylene glycol) etc. In one particular aspect, alkoxylated polyester is formed in this process.

In another particular aspect, an alkoxylated polymer is formed by reacting a poly(alkylene glycol) with one terminal hydroxyl group with a diisocyanate to obtain an isocyanate functional reaction product, and reacting the isocyanate functional reaction product with a hydroxyl functional base polymer at an equimolar ratio to form urethane functional groups at each hydroxyl site on the base polymer. The poly(alkylene glycol) may be poly(ethylene glycol) poly(propylene glycol) etc. In one particular aspect, alkoxylated polyurethane is formed in this process.

In another particular aspect, an alkoxylated polymer is formed by reacting a reacting a poly(alkylene glycol) with one terminal hydroxyl group with a diepoxide to obtain an epoxy functional reaction product, and reacting the epoxy functional reaction product with a hydroxyl functional base polyester at an equimolar ratio to form ether groups at each hydroxyl site on the base polyester. The poly(alkylene glycol) may be poly(ethylene glycol) poly(propylene glycol) etc.

In another particular aspect, an alkoxylated polymer is formed by reacting a poly(alkylene glycol) with one terminal hydroxyl group with a diisocyanate to obtain an isocyanate functional reaction product, and reacting the isocyanate functional reaction product with a hydroxyl functional base polyester at an equimolar ratio to form urethane functional groups at each hydroxyl site on the base polyester. The poly(alkylene glycol) may be poly(ethylene glycol) poly(propylene glycol) etc. In one particular aspect, an alkoxylated polyurethane is formed in this process.

In another particular aspect, an alkoxylated polymer is formed by reacting a poly(alkylene glycol) with one terminal hydroxyl group with a diacid or an acid anhydride to obtain a carboxyl functional reaction product, and reacting the carboxyl functional reaction product with a hydroxyl functional base polyurethane at an equimolar ratio to form ester groups at each hydroxyl site on the base polyurethane. The poly(alkylene glycol) may be poly(ethylene glycol) poly(propylene glycol) etc. In one particular aspect, an alkoxylated polyurethane or polyurethane-urea is formed in this process.

In another particular aspect, an alkoxylated polymer is formed by reacting a poly(alkylene glycol) with one terminal hydroxyl group with a diacid or an acid anhydride to obtain a carboxyl functional reaction product, and reacting the carboxyl functional reaction product with a diepoxide to obtain an epoxy functional reaction product, at an equimolar ratio to form ester groups at each carboxyl site on the base polymer. The poly(alkylene glycol) may be poly(ethylene glycol) poly(propylene glycol) etc. In one particular aspect, an alkoxylated polyester is formed in this process.

In another particular aspect, an alkoxylated polyurethane or polyurethane-urea is formed by reacting a poly(alkylene glycol) with one terminal hydroxyl group with a diisocyanate to obtain an isocyanate functional reaction product, and reacting the isocyanate functional reaction product with a hydroxyl functional base polyurethane or polyurethane-urea at an equimolar ratio to form urethane or urethane-urea functional groups at each hydroxyl site on the base polyurethane or polyurethane-urea. The poly(alkylene glycol) may be poly(ethylene glycol) poly(propylene glycol) etc.

In another particular aspect, an alkoxylated polyurethane or polyurethane-urea is formed by reacting a poly(alkylene glycol) with one terminal hydroxyl group with a diacid or an acid anhydride to obtain a carboxyl functional reaction product, and reacting the carboxyl functional reaction product with a hydroxyl functional base polyurethane at an equimolar ratio to form ester groups at each hydroxyl site on the base polyurethane or polyurethane-urea. The poly(alkylene glycol) may be poly(ethylene glycol) poly(propylene glycol) etc.

The alkoxylated polymers can be used for any purpose for which polymers are generally used, including, but not limited to, primers, inks, or coating compositions, packaging such as bags and bottles, electrical applications such as insulators or conductors on circuit boards, adhesives, protective films, flexible foams, optical elements, etc. Preferably, the alkoxylated polymers are used as additives in primers, inks or coating compositions. Preferred are high speed printing inks. The alkoxylated polymers may, for example, function as dispersants or as low tack binders in the primers, inks, or coating compositions. Advantageously, the alkoxylation of the polymers renders them more compatible with other polymers and resins typically found in primers, inks, or coating compositions. The opacity, gloss, scratch resistance, and laydown of a printing ink can be improved by incorporating the alkoxylated polymer into the printing ink.

DETAILED DESCRIPTION

It is to be understood that the foregoing general description and the following detailed description are exemplary and explanatory only, and are not restrictive of any subject matter claimed.

Unless otherwise defined, all technical and scientific terms used herein have the same meaning as is commonly understood by one of skill in the art to which the inventions belong. All patents, patent applications, published applications and publications, websites and other published materials referred to throughout the entire disclosure herein, unless noted otherwise, are incorporated-by-reference into the present disclosure in their entirety for any purpose.

Definitions

In this application, the use of the singular includes the plural unless specifically stated otherwise. As used herein, the singular forms "a," "an" and "the" are intended to include the plural forms as well, unless the context clearly indicates otherwise.

"Or" means "and/or", unless stated otherwise.

"Comprises" and/or "comprising" specify the presence of the stated features, integers, steps, operations, elements, and/or components, but do not preclude the presence or addition of one or more other features, integers, steps, operations, elements, components, and/or groups thereof. Furthermore, to the extent that the terms "includes," "having," "has," "with," "composed," "comprised" or variants thereof are used in either the detailed description or the claims, such terms are intended to be inclusive in a manner similar to the term "comprising."

Ranges and amounts can be expressed as "about" a particular value or range. "About" is intended to also include the exact amount. For example, "about 5 percent" means "about 5 percent" and also "5 percent" of the thing in issue (e.g., the amount a component is present in weight %). "About" means within typical experimental error for the application or purpose intended.

"Backbone" of a polymer chain is a polymerized sequence of monomer units, the chain thus containing residues of the monomer or monomers that are polymerized.

A "copolymer" is the polymerization product of two or more monomers.

A "pendant" group is a group that is attached to the backbone of a polymer. "Pendant" may be used to describe a group that is actually part of a polymerized monomer unit.

A "terminal end" or "terminal group" is a group located at the end of the polymer chain and is chemically attached to a monomer unit, e.g., the repeating unit of the polymer chain. A terminal end or group may, for example, have a composition distinct from the composition of the backbone of the polymer. A "pendant" group may occur in a "terminal" position. As such, a "terminal" group is a special case of a "pendant" group.

As used herein, the term "laydown" or "lay" in the context of printing refers to the smoothness and evenness of primers, inks, and/or coating compositions. Poor lay or laydown means that the solid print areas of a printed primers, inks, and/or coating compositions are not of a completely uniform film thickness.

"Opacity" or "contrast ratio opacity" of a pigmented primer, ink, or coating refers to its ability to cover the color or color differences of a substrate. Opacity depends on the amount of light that is transmitted through, or reflected from, the surface of the ink. More opaque colorants have a greater tendency to reflect and refract light.

The "gloss" of a primer, ink, or coating composition is a measure of its ability to reflect incident light. It largely depends on whether or not the primer, ink, or coating composition forms a smooth film on the surface of the substrate.

"Di- or higher" when referring to compounds with functional groups means a chemical compound with two or more functional groups with an active hydrogen. Such functional groups include hydroxyl, carboxyl, thiol, amino, epoxy, and imino.

"Tri- or higher functional polyol" refers to a chemical compound with three or more functional hydroxyl groups. A polyol may be a polymer with three or more functional hydroxyl groups.

"Diol" refers to a chemical compound or polymer with two functional hydroxyl groups.

"Additional functional groups" refers to the presence of different functional groups, such as, for example, COOH, in addition to, for example, the functional hydroxyl groups.

The "acid value" is the weight in milligrams of KOH required to neutralize the pendant carboxylate groups in one gram of polymer at 100% solids.

The "hydroxyl value" is a measure of the number of hydroxyl groups present in a polymer. It is expressed as the weight in mg of KOH required to neutralize the hydroxyl groups in one gram of polymer. It is determined by acetylation using acetic anhydride, and titration of the acetic acid and excess anhydride with KOH.

"Polydispersity" or "dispersity" is the measure of the broadness of a molecular weight distribution of a polymer. It is calculated as $M_w/M_n$, wherein $M_w$ is the weight average molecular weight of the polymer, and $M_n$ is the number average molecular weight of the polymer. A polydispersity index ratio of 1 means that all the chain lengths are equal.

"Yield value," is a feature of the non-Newtonian behavior of inks, wherein a distinct shear stress or force is required before any deformation or flow takes place.

"Tg" or "glass transition temperature" is the temperature range where a thermoplastic or thermosetting polymer changes from a hard, rigid or "glassy" state to a more pliable, compliant or "rubbery" state.

As used herein, the terms "poly(alkylene oxide) modified," "alkylene oxide modified," and "alkoxylated" are used interchangeably.

As used herein, the term "aggregate" or "aggregates" when referring to pigments in their dry form are groups of primary pigment particles connected at their face through intermolecular forces.

As used herein, "agglomerate" or "agglomerates" are similar to aggregation, but are groups of primary particles connected at their edges and corners through weaker attractions to each other than aggregates.

As used herein, the term "flocculate" refers to a group of particles that has come back together after dispersion. The attractive forces of primary particles in flocculates are weaker than those of aggregates or agglomerates. The term "to flocculate" means the act of particles coming back together after dispersion. Pigment particles may be susceptible to this effect.

The alkoxylated polymers of the present application comprise a polyalkylene glycol backbone having alkoxylated sites in non-reactive form e.g., non-reactive ether sites, and at least one terminal end that is reactive, where reactions such as etherification (alkoxylation) and esterification may occur. The alkoxylated polymers also comprise a one or more polyfunctional monomers or oligomers having two or more functional groups with active hydrogen. The polyfunctional monomers or oligomers may provide certain functionality to the alkoxylated polymer, such as ester group functionality or urethane group functionality.

By preparing the alkoxylated polymers from materials such as polyalkylene glycol (e.g., polyethylene glycol, polypropylene glycol, polybutylene glycol, block copolymers and terpolymers thereof, etc.), a polymeric structure is provided having one or more non-reactive alkoxylation sites and at least one reactive terminal end, where alkoxylation may occur. Reactions at the terminal ends between the polyfunctional monomers or oligomers take place within the one-step polymerization process, extending chain length and imparting additional functionality to the polymer, e.g., polyester functionality, polyurethane functionality, and polyurethane-urea functionality.

In one aspect, the polyalkylene glycol polymer is selected from polyethylene glycol, polypropylene glycol, polybutylene glycol, and copolymers and terpolymers thereof. In one particular aspect, the polyalkylene glycol polymer is selected from polyethylene glycol, polypropylene glycol, and copolymers of polyethylene glycol and polypropylene glycol.

The polyalkylene glycol may be a monofunctional polyalkylene glycol, e.g., a monofunctional polyethylene glycol or a monofunctional polypropylene glycol. The polyalkylene glycol may be a difunctional polyalkylene glycol, e.g., a difunctional polyethylene glycol or a difunctional polypropylene glycol.

The difunctional polyalkylene glycol may be a block co-polyalkylene glycol having sequences of polyethylene glycol and sequences of polypropylene glycol in a di- or tri-block architecture. The difunctional polyalkylene glycol may be a block co-polyalkylene glycol having sequences of polyethylene glycol and sequences of polypropylene glycol in a tri-block architecture with two blocks of polyethylene glycol and one block of polypropylene glycol. The difunctional polyalkylene glycol may be a block co-polyalkylene glycol having sequences of polyethylene glycol and sequences of polypropylene glycol in a tri-block architecture with one block of polyethylene glycol and two blocks of polypropylene glycol.

In one aspect, the difunctional polyalkylene glycol may be a block copolymer having random sequences of poly (ethylene oxide)-ran-poly(propylene oxide) that is, a copolymer having random sequences of polyethylene glycol and polypropylene glycol.

In another aspect, the difunctional polyalkylene glycol may be a block copolymer of polyalkylene glycol having, for example, sequences of polyethylene glycol and sequences of polypropylene glycol in a tapered copolymer architecture.

The alkoxylated polymers described herein may be, for example, an alkoxylated polyester, an alkoxylated polyurethane, and an alkoxylated polyurethane-urea. In one particular aspect, the one or more polyfunctional monomers or oligomers are (a) one or more diols and/or polyols (e.g., a polyol has more functionality than a diol) and (b) one or more diacids and/or anhydrides. The alkoxylated polymer in this aspect may be an alkoxylated polyester. In another particular aspect, the one or more polyfunctional monomers or oligomers are (a) one or more diols and/or polyols and (b) one or more diisocyanates, or mixtures thereof. The alkoxylated polymer resulting in this aspect is alkoxylated polyurethane.

In one aspect, an alkoxylated polyester further comprises one or more —COOH functional diols, such as a polyester derived in part from a —COOH functional diol such as dimethylolbutanoic acid or dimethylolpropionic acid.

In another aspect, the alkoxylated polyester further comprises one, two or more than two diols. Suitable diols include, for example, 1,4-butanediol, 1,3-propanediol, 1,2-propanediol, pentanediol, hexanediol, 2-methyl-1,3-propanediol, cyclohexyldimethanol, diethylene glycol, triethylene glycol and neopentylglycol.

In another particular aspect, an alkoxylated polymer can be produced using an etherification process or an esterification process. In aspect of an etherification process, a mono- or di-functional polyalkylene oxide glycol is reacted with a monomer or oligomer or polymer having hydroxyl functionality. In one esterification process aspect, a mono- or di-functional polyalkylene glycol is reacted with a carboxylic acid-functional monomer or oligomer or polymer. The mono- or di-functional polyalkylene glycol used in these reactions is preferably mono- or di-functional polyethylene glycol, mono- or di-functional polypropylene glycol, and block copolymers thereof. Examples of monofunctional polyethylene glycols, polypropylene glycols, and block copolymers thereof are those that have one hydroxyl terminal end. The other non-functional terminal end may be, for example, alkyl, e.g., methyl. Examples of difunctional polyethylene glycols, polypropylene glycols, and block copolymers thereof are those that have two hydroxyl terminal ends, e.g., diol functionality.

In another particular aspect, an alkoxylated polymer that can further polymerize in a free-radical reaction scheme such as in an energy-curable primer, ink or coating composition can be produced using an esterification process. In the esterification a di-functional polyalkylene glycol with two hydroxyl groups is reacted with an acrylic acid or (meth) acrylic acid having carboxylic acid-functionality and acrylate functionality, e.g., an unsaturated carbon-carbon bond at a terminal end. The di-functional polyalkylene glycol used in these reactions may be di-functional polyethylene glycol, di-functional polypropylene glycol, and block copolymers thereof.

The polyfunctional monomers or oligomers may have any combination of two or more functional polar groups. The functional groups of any given polyfunctional monomer or oligomer may be independent of each other. Examples of polar functional groups include, but are not limited to, hydroxyl groups, carboxyl groups, anhydride groups, epoxy groups, thiol groups, amino groups, imino groups, isocyanate groups, amido groups, or ureido groups. Anhydride functionality includes two reactive functional groups.

Suitable hydroxyl functional monomers and/or oligomers include any type of monomers and/or oligomers having two or more functional hydroxyl groups. Hydroxyl functional monomers and/or oligomers may contain only hydroxyl functional groups, or other functional groups in addition to the hydroxyl groups. Examples of hydroxyl functional monomers and/or oligomers include, but are not limited to trimethylol propane, ethylene glycol, diethylene glycol, triethylene glycol, 1,4-butanediol, 1,3-propanediol, 1,2-propanediol, hexanediol, 2-methyl-1,3-propanediol, neopentylglycol, cyclohexyldimethanol, diethylene glycol and triethylene glycol, trimethylolethane, pentaerythritol, glycerol, 1,2,4-benzenetriol, 1,3,5-benzenetriol, 1,2,3-benzenetriol, and the like. Preferably, at least one of the polyfunctional monomers and/or oligomers is trimethylol propane.

Suitable carboxyl functional monomers and/or oligomers include any type of monomers and/or oligomers having two or more functional carboxyl groups. Carboxyl functional monomers and/or oligomers may contain only carboxyl functional groups, or other functional groups in addition to the carboxyl groups. Examples of carboxyl functional monomers and/or oligomers include, but are not limited to, acrylic acid, methacrylic acid, itaconic acid, crotonic acid, maleic acid, succinic acid, malonic acid, diethyl malonic acid, monobutyl maleate, 1,3-acetonedicarboxylic acid, azelaic acid, benzylmalonic acid, biphenyl-4,4'-dicarboxylic acid, 1,3,5-cyclohexanetricarboxylic acid, cyclohexylsuccinic acid, and the like.

Suitable thiol functional monomers and/or oligomers include any type of monomers and/or oligomers having two or more functional thiol groups. Thiol functional monomers and/or oligomers may contain only thiol functional groups, or other functional groups in addition to the thiol groups. Examples of thiol functional monomers and/or oligomers include, but are not limited to, trimethylolpropane tris(3-mercaptopropionate); trimethylolpropane tris(2-mercaptoacetate); pentaerythritol tetrakis(2-mercaptoacetate); pentaerythritol tetrakis(3-mercaptopropionate); 2,2'-(ethylenedioxy)diethanethiol; 1,3-propanedithiol; 1,2-ethanedithiol; 1,4-butanedithiol; tris[2-(3-mercaptopropionyloxy)ethyl] isocyanurate; and 3,4-ethylenedioxythiophene, and the like.

Suitable amino functional monomers and/or oligomers include monomers and/or oligomers having two or more functional amino groups. Amino functional monomers and/or oligomers may contain only amino functional groups, or other functional groups in addition to the amino groups. Examples of amino functional monomers and/or oligomers include, but are not limited to, m-phenylenediamine, p-phenylenediamine, methylene dianiline, hydrogenated methylene dianiline, durene diamine, 1,3,5-triaminobenzene, 1,3,4-triaminobenzene, 3,5-diaminobenzoic acid, 2,4-diaminotoluene, 2,4-diaminoanisole, and xylylenediamine, ethylenediamine, propylenediamine, and tris (2-diaminoethyl) amine, and the like.

Suitable imino functional monomers and/or oligomers include monomers and/or oligomers that have two or more functional imino groups. Imino functional monomers and/or oligomers may contain only imino functional groups, or other functional groups in addition to the imino groups. Examples of imino functional monomers and/or oligomers include, but are not limited to, bis(imino)pyridine; 3,3'-iminodipropionitrile; [2,6-bis(1-phenylimino)ethyl]pyridine, and the like.

Suitable amido functional monomers and/or oligomers include monomers and/or oligomers that have two or more functional amido groups. Amido functional monomers and/or oligomers may contain only amido functional groups, or other functional groups in addition to the amido group.

Suitable ureido functional monomers and/or oligomers include monomers and/or oligomers that have two or more ureido functional groups. Ureido functional monomers and/or oligomers may contain only ureido functional groups, other functional groups in addition to the ureido functional groups. Examples of ureido functional monomers include, but are not limited to, dimethylbis(ureido)silane, ureidopyrimidinone, and the like.

Suitable diepoxide monomers include 1,3-butadiene diepoxide and diepoxybutane.

The alkoxylated polymers may be functionalized by one or more diacids, anhydrides, and mixtures thereof. Suitable diacids include, but are not limited to, adipic acid, phthalic acid, terephthalic acid, maleic acid, isophthalic acid, sebacic acid, azelaic acid, fumaric acid, 1,4-cyclohexanedicarboxylic acid, dimethyl terephthalate, and the like. Suitable anhydrides include, but are not limited to dimethyl isophthalate tetrahydrophthalic anhydride, hexahydrophthalic anhydride, phthalic anhydride, trimellitic anhydride, maleic anhydride, succinic anhydride, and the like. Preferably, the anhydride is tetrahydrophthalic anhydride.

The alkoxylated polymers may be functionalized by one or more —COOH functional diols. Examples of —COOH functional diols include, but are not limited to dimethylolpropionic acid and dimethylolbutanoic acid.

In one aspect of the present disclosure, the alkoxylated polymers described herein may be synthesized using amounts of monofunctional endcappers such as methanol, ethanol, propanol, butanol, 1-dodecanol and poly(alkylene glycol) monobutyl ether to avoid gelation at high conversions, particularly when a monomer or oligomer is used having functionality greater than 2, which could otherwise result in gelation.

The alkoxylation of polymeric materials can occur in a number of different ways, several of which are described in co-pending, commonly owned International Patent Application No. PCT/US2015/031949, filed May 21, 2015, which is incorporated herein by reference in its entirety.

In one aspect, a linear diol that contains an alkoxylation site in a non-reactive form may be used in forming the alkoxylated polymers. The linear diol may be a linear polymeric diol, such as polypropylene glycol, a polyethylene glycol, and copolymers thereof with hydroxyl end groups. Diethylene glycol and neopentyl glycol exemplify linear monomeric diols containing an alkoxylation site in a non-reactive form. The hydroxyl end groups undergo a reaction with suitable polyfunctional monomers and oligomers to incorporate the linear diol into the alkoxylated polymer in a single step. Depending on the monomers, the reaction may be an etherification, and it may be an esterification.

Other monomeric glycols, such as low molecular weight short-chain diols could also be used forming the alkoxylated polymers described herein. Exemplary monomeric glycols include ethylene glycol, 1,4-butanediol, 1,3-propanediol, 1,2-propanediol, pentanediol, hexanediol, 2-methyl-1,3-propanediol, cyclohexyldimethanol, diethylene glycol and triethylene glycol.

Oligomeric glycols may be used, such as hydroxyl-terminated polyethylene glycols of about 200 to about 500,000 Daltons, hydroxyl-terminated polypropylene oxides of molecular weight ranges of about 200 to about 50,000 Daltons and mixed hydroxyl-terminated polyethylene-polypropylene glycol oligomers of about 200 to about 50,000 Daltons.

In another aspect, a linear diol that contains an alkoxylation site in a non-reactive form may be reacted with a suitable diisocyanate monomer to incorporate the alkoxylated monomer in a single step.

In one aspect, the alkoxylation is one of an ethoxylation, a propoxylation, or a butoxylation.

In another aspect of the present disclosure, primers, inks, or coating compositions that include the alkoxylated polymers are described herein. The inclusion of an alkoxylated polymer in such compositions is believed to improve compatibility of the resins and components of the primers, inks, or coating compositions with each other, such as by dispersing the components uniformly throughout the composition. Occasionally, one or more polymers or resins in such compositions do not work well together. The compatibility is significantly improved when compared to compositions that do not include alkoxylated polymers.

When the present alkoxylated polymers are included in a primer composition, such as, for example, as a dispersant in a primer composition, they stabilize clays, crosslinking agents, adhesion promoters, etc. present in the primer composition used to prepare the substrate to which improve the adhesion, gloss, etc., of the primer composition.

In particular, the alkoxylated polymers are useful as dispersing agents and as low-tack binders in primers, inks, or coating compositions. The alkoxylated polymers described herein, when added to printing inks, primers, or coating compositions, improve properties of same. Colored flexographic and gravure printing inks that include the alkoxylated polymers described herein have higher opacity and have viscosity that is comparable to commercially available printing inks. The alkoxylated polymers for use as dispersants, low-tack binders, etc. may be alkoxylated polyesters, alkoxylated polyurethanes, and alkoxylated polyurethane-ureas. The dispersion of pigments is greatly improved when the alkoxylated dispersing agents described herein are included in the primers, inks, or coating compositions.

Printing inks, primers, or coating compositions that include the alkoxylated polymers described herein may have lower viscosity than commercially available printing inks while providing equal opacity. In the case of primers, printing inks or coating compositions that contain colorants other than white (or in combination with white colorants), the printing inks of the present invention exhibit lower viscosity and improved laydown versus primers, printing inks or coating compositions that do not contain the alkoxylated polymers of the present invention.

In one aspect, the primers, inks, or coating compositions described herein, e.g., the primers, inks, or coating compositions that include alkoxylated polyesters, alkoxylated urethanes, and alkoxylated polyurethane-ureas, may be conventional ink vehicles.

The alkoxylated polymers described herein may be incorporated into primers, inks, or coating compositions in any suitable amount. In one aspect, the alkoxylated polymer may be present in primers, inks, or coating compositions in an amount of about 0.01 wt % to about 25 wt %. In another aspect the alkoxylated polymer may be present in primers, inks, or coating compositions in an amount of about 0.1 wt % to about 20 wt %. In yet another aspect, the alkoxylated polymer may be present in primers, inks, or coating compositions in an amount of about 0.1 wt % to about 11 wt %. In still yet another aspect, the alkoxylated polymer may be present in primers, inks, or coating compositions in an amount of about 4.0 wt % to about 15 wt %.

Where the alkoxylated polymer is an alkoxylated polyurethane or an alkoxylated polyurethane-urea, the polymer may be present in primers, inks, or coating compositions in an amount of about 0.1 wt % to about 20 wt %, preferably 0.1 wt % to about 11 wt %.

In addition to including the alkoxylated polymers described herein, e.g., alkoxylated polyesters, alkoxylated urethanes, and alkoxylated polyurethane-ureas, the primers, inks, or coating compositions may further include a colorant, such as, for example, a colorant chosen from organic and inorganic pigments and dyes, and combinations thereof. Such primers, inks, or coating compositions may be any possible color, such as white for example.

Dyes suitable for use as colorant include, but are not limited to, azo dyes, anthraquinone dyes, xanthene dyes, azine dyes, and combinations thereof. Organic pigments may be one pigment or two or more pigments in combination, such as for example Pigment Yellow Numbers 12, 13, 14, 17, 74, 83, 114, 126, 127, 174, 188; Pigment Red Numbers 2, 22, 23, 48:1, 48:2, 52, 52:1, 53, 57:1, 112, 122, 166, 170, 184, 202, 266, 269; Pigment Orange Numbers 5, 16, 34, 36; Pigment Blue Numbers 15, 15:3, 15:4; Pigment Violet Numbers 3, 23, 27; and/or Pigment Green Number 7. Inorganic pigments may be selected from, for example: iron oxides, titanium dioxides, chromium oxides, ferric ammonium ferrocyanides, ferric oxide blacks, Pigment Black Number 7 and/or Pigment White Numbers 6 and 7. Other organic and inorganic pigments and dyes can also be employed, as well as combinations that achieve the colors desired. The primers, inks, or coating compositions may be any known color, e.g., black, white, red, orange, yellow, green, blue, indigo, violet and all shades and combinations in between.

Additives may be incorporated into the primers, inks, or coating compositions described herein to enhance various properties of the compositions. A partial list of such additives include, but is not limited to adhesion promoters, light stabilizers, de-gassing additives, flow promoters, defoamers, antioxidants, UV stabilizers, surfactants, dispersants, plasticizers, rheological additives, waxes, silicones, and others.

The primers, inks or coating compositions described herein that contain the alkoxylated polymers may be printed by any known printing technique. For example, the compositions may be printed by flexography, in which case the composition is a flexographic one. The composition may be printed by lithography, in which case the composition is a lithographic one. The composition may be printed by gravure, in which case the composition is a gravure one. The composition may be printed by offset, in which case the composition is an offset one. The composition may be printed by screen printing, in which case the composition is a screen printing one.

The primers, inks, or coating compositions described herein that contain the alkoxylated polymers (e.g., alkoxylated polyesters, alkoxylated urethanes, and alkoxylated polyurethane-ureas) may also include energy-curable components, such as one or more energy-curable acrylate resins. The energy curable compositions may be cured by exposure to UV-radiation, in which instance the primers, inks, or coating compositions may further include one ore more photoinitiator components to initiate the energy curing of the acrylate resin.

In a particular aspect, provided is an alkoxylated polyester comprising a polyalkylene glycol component having one or more alkoxylated sites in a non-reactive form and at least one reactive terminal end, one or more diacids and/or acid anhydrides; and one or more diols or higher functional polyols. In another particular aspect, the polyalkylene glycol component of the alkoxylated polyester comprises a component selected from polyethylene glycol, polypropylene glycol, and block copolymers thereof. In a further particular aspect, the alkoxylated polyester comprises one or more —COOH functional diols. In another particular aspect, the alkoxylated polyester further comprises one or more additional diols.

In yet another particular aspect, the alkoxylated polyester is alkoxylated in an esterification process. The esterification of the alkoxylated polyester may occur by reacting a monofunctional polyalkylene glycol with a carboxylic acid functional polyester. Examples of monofunctional polyalkylene glycols include monofunctional polyethylene glycols and polypropylene glycols having one hydroxyl terminal end. The other non-functional terminal end may be, for example, alkyl, e.g., methyl.

The alkoxylation of the polyester may have the effect of improving compatibility of the polyester with one or more other resins in the primers, inks or coating compositions.

The alkoxylated polymers described herein may be produced in a one-step process in which the monomers, oligomers and polymers used to produce the alkoxylated polymers are added to a reaction vessel and polymerization is commenced, e.g., by heating the vessel and its contents.

In a particular aspect, the present invention provides an alkoxylated polyurethane comprising a polyalkylene glycol component having one or more alkoxylated sites in a non-reactive form and at least one reactive terminal end; one or more diisocyanates; and one or more diols or polyols. In another particular aspect, the polyalkylene glycol component comprises a component selected from polyethylene glycol, polypropylene glycol, and block copolymers thereof. In another particular aspect, the polyurethane or polyurethane-urea further comprises one or more —COOH functional diols. In another particular aspect, the alkoxylated polyurethane or polyurethane-urea further comprises one or more additional diols. In yet another particular aspect, the alkoxylated polyurethane or polyurethane-urea is alkoxylated in an esterification process. The esterification of the polyurethane may occur by reacting a monofunctional polyalkylene oxide glycol with a carboxylic acid functional polyurethane or polyurethane-urea.

In the esterification of the alkoxylated polyurethane or polyurethane-urea, the monofunctional polyalkylene glycol may be selected from, for example, monofunctional polyethylene glycol, monofunctional polypropylene glycol, and block copolymers thereof. Examples of monofunctional polyalkylene glycols include monofunctional polyethylene glycols and polypropylene glycols having one hydroxyl terminal end. The other non-functional terminal end may be, for example, alkyl, e.g., methyl.

The alkoxylation of the polyurethane or polyurethane-urea may have the effect of improving compatibility of the polyurethane or polyurethane-urea with one or more other resins in the primers, inks, or coating compositions.

In one embodiment, the alkoxylation of the polymer, e.g., the alkoxylation of the polyester, the polyurethane, or the polyurethane-urea incorporates one of ethoxy, propoxy and butoxy units within the polymer. In other words, the alkoxylation is selected from the group consisting of propoxylation, ethoxylation, and butoxylation.

In a particular aspect, the present invention provides a printing ink comprising the alkoxylated polymer, and at least one colorant; wherein the alkoxylated polymer comprises a polyalkylene glycol component having one or more alkoxylated sites in a non-reactive form and at least one reactive terminal end; wherein the alkoxylated polymer further comprises one or more polyfunctional monomers or oligomers, or mixtures thereof, wherein each monomer or oligomer has two or more functional polar groups with active hydrogen.

In a particular aspect, the presence of the alkoxylated polymers described herein in a printing ink may improve the opacity, gloss, scratch resistance, and/or laydown of the ink.

The alkoxylated polymers described herein, such as alkoxylated polyesters, alkoxylated polyurethanes and alkoxylated polyurethane-ureas, are useful as additives in primers, inks, or coating compositions. For example, the alkoxylated polymers are useful as dispersants and as low tack binders in such compositions. The alkoxylated polymers enable one skilled in the art to formulate primers, printing inks, or coating compositions having various improved properties. In the case of white flexographic and white gravure printing inks, the printing inks of the present disclosure exhibit higher opacity at a viscosity which is comparable to commercially available printing inks. Also, printing inks of the invention may have lower viscosity than commercially available printing inks at equal or comparable opacity. In the case of printing inks that contain colorants other than white (or in combination with white colorants), the printing inks of the present invention exhibit lower viscosity and improved laydown versus printing inks that do not contain the alkoxylated polymers of the present invention.

The alkoxylated polymers described herein may be used as a dispersant or low tack binder in all types of primers, inks, or coating compositions, including but not limited to solvent-based, water-based and energy-curable printing ink formulations. While the primers, printing inks or coating compositions described herein may be printed in any kind of printing process, e.g., flexographic, lithographic, offset, gravure, and screen printing, they are well suited for making flexographic and gravure printing ink formulations.

EXAMPLES

The following examples illustrate specific aspects of the present invention and are not intended to limit the scope thereof in any respect and should not be so construed.
Test Methods and Equipment Molecular weights and polydispersity values were measured via Gel Permeation Chromatography (GPC) in a suitable solvent using a Viscolite 700 viscometer obtained from Hydramotion Co equipped with a Waters 2410 refractive index detector or equivalent with Waters Millennium chromatography software version 3.0 or equivalent, with a Phenogel GPC 5 column set 300×7.8 mm OD, 5μ particle size (Phenomenex) and pore sizes of 50 Å, 100 Å, 500 Å, $10^3$ Å and $10^4$ Å.

Film formation: Inks were coated onto clear polyethylene film using a Phantom proofer (Harper) 6.8 volume 200 line anilox. The films were air dried at 43° C. for 60 seconds.

Opacity was measured using a BNL-3 Opacimeter by Technidyne, set on opacity readings.

Adhesion was measured by the 610 scotch tape test according to ASTM F2252-03.

Gloss was measured using a BYK-Micro Tri Gloss at an angle of 60 degrees.

Scratch resistance was measured by scratching the printed ink or coating with the back of a fingernail (10 scratches).

Wear was measured with the Sutherland Rub Tester using 100 rubs with a 4 pound test strip.

Laydown was assessed by optical microscopy using bright field illumination.

Particle size measurements were made at 25° C. on a Laser Light Scattering (LLS) instrument, model LB 500 manufactured by Horiba.

Example 1: Synthesis of A Linear Alkoxylated Polyester

An alkoxylated hydroxyl functional polyester was synthesized according to the following procedure.

12.5 g (0.0124 moles) of Pluracol® 1010, 33.9 g (0.31 moles) of diethylene glycol obtained from Sigma-Aldrich, and 26.5 g (0.31 moles) of tetrahydrophthalic anhydride, obtained from Reichhold, were weighed into a 250 ml 4-necked round bottom flask equipped with a heating mantle, overhead stirrer, temperature sensor, gas inlet, and Dean-Stark trap with a condenser. The temperature was raised to 100° C. under a nitrogen atmosphere and 0.2 g p-toluene sulfonic acid monohydrate as catalyst (0.001 moles, Sigma-Aldrich) was added. The reaction was raised to 160-190° C. for six hours. The alkoxylated polymer resin that was produced had Mw of 1500 Daltons.

Pluracol® 1010 is a polypropylene glycol diol formed from adding propylene oxide to a propylene glycol nucleus. Pluracol® 1010 has a molecular weight (Mw) of 1010 Daltons and is commercially available from BASF.

Example 2: Synthesis of Another Linear Alkoxylated Polyester 12.5 g of Pluracol® 1010 (0.0124 moles), 33.9 g of diethylene glycol (0.31 moles), and 26.5 g of tetrahydrophthalic anhydride (0.31 moles) were weighed into a 250 ml 4-necked round bottom flask equipped with a heating mantle, overhead stirrer, temperature sensor, gas inlet, and a Dean-Stark trap with a condenser. The reaction was heated to 100° C. under a nitrogen atmosphere and 0.4 g p-toluene sulfonic acid monohydrate as catalyst (0.002 moles, Sigma-Aldrich) was added. The reaction was heated to 160-190° C. for 6 hours. The alkoxylated polymer resin that was produced had Mw of 3610 Daltons.

The alkoxylated polyesters in Examples 1 and 2 were synthesized "neat" (without solvents). They could also be synthesized in the presence of one or more solvents. Examples of suitable solvents that could be used in the synthesis include, but are not limited to, petroleum solvents (e.g. heptane) and ethers (e.g. tetrahydrofuran, and 1,4-dioxane) and the like.

Example 3: Alkoxylated Polymer from PEG-PPG-PEG Block Copolymer 13.6 g of a PEG-PPG-PEG block copolymer with —OH group functionality at each terminal end and having 1100 Daltons Mw (0.0124 moles) that is obtained from Sigma-Aldrich, 33.9 g of diethylene glycol (0.31 moles), and 26.5 g of tetrahydrophthalic anhydride (0.31 moles) were weighed into a 250 ml 4-necked round bottom flask equipped with a heating mantle, overhead stirrer, temperature sensor, gas inlet, and a Dean-Stark trap with a condenser. The reaction was heated to 100° C. under a nitrogen atmosphere and 0.4 g p-toluene sulfonic acid monohydrate (0.002 moles) as catalyst was added. The reaction was heated to 160-190° C. for 6 hours. The alkoxylated polymer resin that was produced was soft and tacky and had Mw of 3860 Daltons.

Example 4

13.6 g of a PEG-PPG-PEG block copolymer with —OH group functionality at each terminal end and having 1100 Daltons Mw (0.0124 moles) that is obtained from Sigma-Aldrich, 33.2 g of neopentyl glycol (0.31 moles, Sigma-Aldrich), and 46.2 g of phthalic anhydride (0.31 moles, Sigma-Aldrich) were weighed into a 250 ml 4-necked round bottom flask equipped with a heating mantle, overhead stirrer, temperature sensor, gas inlet, and a Dean-Stark trap with a condenser. The reaction was heated to 100° C. under a nitrogen atmosphere and 0.4 g p-toluene sulfonic acid monohydrate (0.002 moles, Sigma-Aldrich) as catalyst was added. The reaction was heated to 170-180° C. for 6 hours. The alkoxylated polymer resin that was produced was soft and tacky and had Mw of 1710 Daltons.

Example 5

13.6 g of a PEG-PPG-PEG block copolymer with —OH group functionality at each terminal end and having 1100 Daltons Mw (0.0124 moles) that is obtained from Sigma-Aldrich, 33.2 g of neopentyl glycol (0.31 moles, Sigma-Aldrich), and 48.7 g of phthalic anhydride (0.33 moles, Sigma-Aldrich) were weighed into a 250 ml 4-necked round bottom flask equipped with a heating mantle, overhead stirrer, temperature sensor, gas inlet, and a Dean-Stark trap with a condenser. The reaction was heated to 100° C. under a nitrogen atmosphere and 0.4 g p-toluene sulfonic acid monohydrate (0.002 moles, Sigma-Aldrich) as catalyst was added. The reaction was heated to 170-180° C. for 6 hours. The alkoxylated polymer resin that was produced was soft and had Mw of 2850 Daltons.

Example 6

13.6 g of a PEG-PPG-PEG block copolymer with —OH group functionality at each terminal end and having 1100

Daltons Mw (0.0124 moles) that is obtained from Sigma-Aldrich, 33.2 g of neopentyl glycol (0.31 moles, Sigma-Aldrich), and 54.5 g of isophthalic anhydride (0.33 moles, Sigma-Aldrich) were weighed into a 250 ml 4-necked round bottom flask equipped with a heating mantle, overhead stirrer, temperature sensor, gas inlet, and a Dean-Stark trap with a condenser. The reaction was heated to 100° C. under a nitrogen atmosphere and 0.4 g p-toluene sulfonic acid monohydrate (0.002 moles, Sigma-Aldrich) as catalyst was added. The reaction was heated to 170-180° C. for 7 hours. The alkoxylated polymer resin that was produced was soft and tacky and had Mw of 2210 Daltons.

Example 7

13.6 g of a PEG-PPG-PEG block copolymer with —OH group functionality at each terminal end and having 1100 Daltons Mw (0.0124 moles) that is obtained from Sigma-Aldrich, 54.1 g of neopentyl glycol (0.52 moles, Sigma-Aldrich), 54.5 g of isophthalic anhydride (0.33 moles, Sigma-Aldrich), and 29.6 g of phthalic anhydride (0.20 moles, Sigma-Aldrich) were weighed into a 250 ml 4-necked round bottom flask equipped with a heating mantle, overhead stirrer, temperature sensor, gas inlet, and a Dean-Stark trap with a condenser. The reaction was heated to 100° C. under a nitrogen atmosphere and 0.4 g p-toluene sulfonic acid monohydrate (0.002 moles, Sigma-Aldrich) as catalyst was added. The reaction was heated to 170-180° C. for 7 hours. The alkoxylated polymer resin that was produced had Mw of 3660 Daltons. Example 7 represents a lower percentage of propoxylation (lower weight % of polypropylene glycol in the starting block copolymer, and conversely, greater weight % of polyethylene glycol).

Example 8

71.9 g of a PEG-PPG-PEG block copolymer with —OH group functionality at each terminal end and having 5800 Daltons Mw (0.0124 moles) that is obtained from Sigma-Aldrich, 33.2 g of neopentyl glycol (0.31 moles, Sigma-Aldrich), and 48.7 g of phthalic anhydride (0.32 moles, Sigma-Aldrich) were weighed into a 250 ml 4-necked round bottom flask equipped with a heating mantle, overhead stirrer, temperature sensor, gas inlet, and a Dean-Stark trap with a condenser. The reaction was heated to 100° C. under a nitrogen atmosphere and 0.4 g p-toluene sulfonic acid monohydrate (0.002 moles, Sigma-Aldrich) as catalyst was added. The reaction was heated to 170-190° C. for 6 hours. The alkoxylated polymer resin that was produced had Mw of 7510 Daltons. Example 8 represents higher percentage of propoxylation, using a higher Mw PEG-PPG-PEG block copolymer diol (greater weight % of polypropylene glycol; lesser weight % of polyethylene glycol).

Example 9

13.6 g of a PEG-PPG-PEG block copolymer with —OH group functionality at each terminal end and having 1100 Daltons Mw (0.0124 moles) that is obtained from Sigma-Aldrich, 33.9 g of diethylene glycol (0.31 moles, Sigma-Aldrich) and 46.2 g of phthalic anhydride (0.31 moles, Sigma-Aldrich) were weighed into a 250 ml 4-necked round bottom flask equipped with a heating mantle, overhead stirrer, temperature sensor, gas inlet, and a Dean-Stark trap with a condenser. The reaction was heated to 100° C. under a nitrogen atmosphere and 0.4 g p-toluene sulfonic acid monohydrate (0.002 moles, Sigma-Aldrich) as catalyst was added. The reaction was heated to 175-180° C. for 6 hours. The alkoxylated polymer resin that was produced had Mw of 2360 Daltons.

Example 10

71.9 g of a PEG-PPG-PEG block copolymer with —OH group functionality at each terminal end and having 5800 Daltons Mw (0.0124 moles) that is obtained from Sigma-Aldrich, 33.2 g of diethylene glycol (0.31 moles, Sigma-Aldrich), and 46.2 g of phthalic anhydride (0.31 moles, Sigma-Aldrich) were weighed into a 250 ml 4-necked round bottom flask equipped with a heating mantle, overhead stirrer, temperature sensor, gas inlet, and a Dean-Stark trap with a condenser. The reaction was heated to 100° C. under a nitrogen atmosphere and 0.4 g p-toluene sulfonic acid monohydrate (0.002 moles, Sigma-Aldrich) as catalyst was added. The reaction was heated to 175-180° C. for 6 hours. The alkoxylated polymer resin that was produced had Mw of 3610 Daltons.

Example 11

A hybrid alkoxylated hydroxyl functional polyester may be synthesized according the formulation below in Table 1. Example 11 is a prophetic example including components A and C, described in co-pending, commonly owned International Patent Application No. PCT/US2015/031949, filed May 21, 2015 and component B, a polyethylene glycol—polypropylene glycol—polyethylene glycol block copolymer as described herein, having 1100 Daltons Mw, with reactive —OH terminal ends.

TABLE 1

| | Material | (%) |
|---|---|---|
| A | Trimethylol propane | 36.5 |
| B | Polyethylene glycol - Polypropylene glycol - Polyethylene glycol 1100 | 17.5 |
| C | Tetrahydrophthalic anhydride | 52.4 |
| D | Water-decanted from condensation polymerization | −6.4 |
| | Total | 100.00 |

Components A, B, and C are added to a thoroughly cleaned and purged reactor. The reactor is then purged with nitrogen and the temperature brought to about 170° C. over 1 hour. The temperature of the reactor is slowly brought to 217° C., and the condenser temperature was not allowed to exceed 100° C. Water formed as a result of the polymerization reaction is removed via a decanter D. The reaction is continued at 217° C. until the acid value is below 7. Once the acid value is below 7, the reaction mixture is filtered and discharged, and cooled to 135° C., and the alkoxylation reaction (more specifically here propoxylation) is begun.

As in other examples comprising the inventive alkoxylated polymers of the present invention, an ink made with prophetic Example 11 alkoxylated polymer would be expected to exhibit improved laydown and in some cases, improved opacity.

Example 12: Experimental Ink Formulations

Experimental ink formulations were prepared, having the compositions indicated in Table 2.

TABLE 2

Example 12 Experimental White Inks

| Material | Ex. 12A (comparative) | Ex. 12B (inventive) | Ex. 12C (inventive) |
|---|---|---|---|
| Polyamide | 13.65 | 13.65 | 13.65 |
| BYK-501 dispersant | 0.3 | | |
| Example 8 Alkoxylated Polymer | | 0.3 | |
| Example 10 Alkoxylated Polymer | | | 0.3 |
| $TiO_2$ | 56.1 | 56.1 | 56.1 |
| Akawax (erucamide) | 0.4 | 0.4 | 0.4 |
| Alcohol (n-propanol) | 24.2 | 24.2 | 24.2 |
| Acetate (n-propyl acetate) | 5.15 | 5.15 | 5.15 |
| Slip additive (wax) | 0.2 | 0.2 | 0.2 |
| TOTAL | 100 | 100 | 100 |

Example 12A, the comparative ink, is a commercially available white ink from Sun Chemical Company, Parsippany N.J.

The inks were coated onto clear polyethylene film using a Phantom proofer (Harper) 6.8 volume 200 line anilox, a printing method used to provide a measured amount of ink to a flexo printing plate. An anilox roll is a hard cylinder, usually constructed of a steel or aluminum core which is coated by an industrial ceramic having a surface provided with millions of very fine dimples, known as cells. The films were air dried at 43° C. for 60 seconds. Each of the inks were tested for viscosity using a Viscolite model 700 (Hydramotion) and for opacity with a BNL-3 Opacimeter (Technidyne). Viscosity of the undiluted ink was measured. The amount of solvent (%) required to reduce the inks to printing viscosity (i.e. 60 cps) is indicated in Table 3. The solvent used was a mixture of 80/20 n-propyl alcohol to n-propyl acetate. The inks were printed at 60 cps, and opacity of the dried inks measured. The results are shown in Table 3.

TABLE 3

Opacity of the White Inks

| | Ex. 12A (comparative) | Ex. 12B (inventive) | Ex. 12C (inventive) |
|---|---|---|---|
| Viscosity | | | |
| Uncut (cps) | 165.5 | 233.7 | 224.8 |
| % solvent required to reduce viscosity to 60 cps | 15 | 16 | 16 |
| Opacity | 53 | 53 | 53 |

The opacity of the inks of Examples 12A, 12B, and 12C was equal. Primers, inks or coating compositions comprising the alkoxylated polymers of the present disclosure exhibit decreased particle size in the resultant pigment dispersions (see Table 4) which will result in better laydown, as was observed in direct visual comparisons with comparative inks. In some cases, improved opacity may also be observed.

The particle size of the comparative ink of Example 12A was measured as is, and with the addition of 2 wt % of the alkoxylated polymeric dispersing agents of Examples 8 and 10. Particle size measurements were made at 25° C. on a Laser Light Scattering (LLS) instrument, model LB 500 manufactured by Horiba, using SL-800 ink as the standard. Results are shown in Table 3.

TABLE 4

Median particle size of reference ink alone, and with Examples 8 and 10 added.

| | Example 12A alone | Example 12A + 2.0% Ex. 8 | Example 12A + 2.0% Ex. 10 |
|---|---|---|---|
| Median particle size (nm) | 1460 | 1200 | 1111 |

Particle size comparison shows a reduction in particle size when the alkoxylated polymer dispersing agents of Examples 8 and 10 are added to the Example 12A ink formulation. The particle size of the Example 12A ink formulation without either of these alkoxylated polymers as a dispersing agent is considerably larger. Particle size was reduced from about 1460 nm to about 1100 to about 1200 nm.

Primers, inks, or coating compositions comprising the alkoxylated polymers as described herein provide decreased particle size as seen in Table 4. The finer pigment dispersions that result translate into better laydown and in general, improved opacity. Moreover, the process of preparing the alkoxylated polymers as described herein is reduced from a 2-step process to a 1-step process, thereby providing improved manufacturing efficiency.

In another embodiment, ink compositions may include alkoxylated polymers, such as those of Example 8 or Example 10, to produce printing inks including colorants other than a white colorant or $TiO_2$. The printing ink would have increased opacity and/or color strength vs. commercial printing inks at reduced particle size.

Example 13

A comparative solvent-based flexographic magenta printing ink was prepared according to the formulation in Table 5.

TABLE 5

Comparative Solvent-Based Flexographic Magenta Printing Ink

| Material | Amount (%) |
|---|---|
| Slow Lithol Rubine base | 50 |
| Polyurethane varnish | 40 |
| 80/20 N-propanol/propyl acetate | 10 |
| Total | 100 |

The printing ink of Example 13 is a highly thixotropic printing ink, with a yield value of 1500 dynes/cm (as measured on a TA Instruments AR1500 rheometer at 25.0° C.).

Example 14

A solvent-based flexographic magenta printing ink including an alkoxylated polymer as described herein was prepared according to the formulation in Table 6.

TABLE 6

Solvent-Based Flexographic Magenta Printing Ink
(Present Description)

| Material | % |
|---|---|
| Slow Lithol Rubine base | 50 |
| Polyurethane varnish | 39 |
| Example 1 Alkoxylated Functional Polyester | 1 |
| 80/20 N-propanol/propyl acetate | 10 |
| Total | 100 |

The printing ink of Example 14 exhibited a reduced yield value (down to 400 dynes/cm. using the same test method as described in Example 13). This resulted in superior laydown for the Example 14 printing ink (assessed visually) when compared to the printing ink of Example 13.

Examples 13 and 14 show that the addition of an alkoxylated polyester (in this case propoxylated polyester) to a solvent based flexographic magenta printing ink reduces viscosity and improves laydown of the printing ink.

The alkoxylated dispersing agents and compositions including same that are the subject of this disclosure have been described above in detail. It will be appreciated that those skilled in the art, upon consideration of the present disclosure, may make modifications and/or improvements on this invention that fall within the scope and spirit of what is described herein.

What is claimed is:

1. An alkoxylated polymer deriving from components comprising:
   a polyalkylene glycol polymer or copolymer backbone having one or more alkoxylated sites in a non-reactive form and at least one reactive terminal end; and
   one or more polyfunctional monomers or oligomers having two or more functional polar groups with an active hydrogen thereof, or mixtures thereof,
   wherein the alkoxylated polymer is polymerized in a one step process, wherein the polyalkylene glycol component is selected from copolymers and terpolymers of polyethylene glycol, polypropylene glycol, and polybutylene glycol.

2. The alkoxylated polymer of claim 1, wherein the at least one reactive terminal end is a site for an alkoxylation.

3. The alkoxylated polymer of claim 1, wherein the one or more polyfunctional monomers or oligomers have functional polar groups independently selected from hydroxyl, carboxyl, anhydride, thiol, amino, epoxy, imino, isocyanate, amido, or ureido.

4. The alkoxylated polymer of claim 1, wherein one or more polyfunctional monomers or oligomers have at least one hydroxyl group; and/or wherein one or more of the polyfunctional monomers and/or oligomers is a diol; and/or wherein one or more of the polyfunctional monomers and/or oligomers are two or more diols; and/or wherein one or more of the polyfunctional monomers and/or oligomers is a —COOH functionalized diol; and/or wherein one or more of the polyfunctional monomers and/or oligomers is a diacid, an acid anhydride, and/or mixtures thereof; and/or wherein one or more of the polyfunctional monomers and/or oligomers is a diisocyanate.

5. The alkoxylated polymer of claim 1, wherein the one or more polyfunctional monomers or oligomers is selected from the group consisting of trimethylol propane, ethylene glycol, diethylene glycol, propylene glycol, 1,4-butanediol, 1,2-propanediol, 1,3-propanediol, pentanediol, hexanediol, 2-methyl-1,3-propanediol, cyclohexyldimethanol, diethylene glycol, triethylene glycol, neopentylglycol, trimethylolethane, pentaerythritol, glycerol, dimethylolbutanoic acid, dimethylolpropionic acid, 1,2,4-benzenetriol, 1,3,5-benzenetriol, 1,2,3-benzenetriol, acrylic acid, methacrylic acid, itaconic acid, crotonic acid, maleic acid, succinic acid, malonic acid, diethyl malonic acid, monobutyl maleate, 1,3-acetonedicarboxylic acid, benzylmalonic acid, biphenyl-4,4'-dicarboxylic acid, 1,3,5-cyclohexanetricarboxylic acid, cyclohexylsuccinic acid, trimethylolpropane tris(3-mercaptopropionate); trimethylolpropane tris(2-mercaptoacetate); pentaerythritol tetrakis(2-mercaptoacetate); pentaerythritol tetrakis(3-mercaptopropionate); 2,2'-(ethylenedioxy)diethanethiol; 1,3-propanedithiol; 1,2-ethanedithiol; 1,4-butanedithiol; tris[2-(3-mercaptopropionyloxy)ethyl] isocyanurate; 3,4-ethylenedioxythiophene, m-phenylenediamine, p-phenylenediamine, 1,3,5-triaminobenzene, 1,3,4-triaminobenzene, 3,5-diaminobenzoic acid, 2,4-diaminotoluene, 2,4-diaminoanisole, xylylenediamine, ethylenediamine, propylenediamine, tris (2-diaminoethyl) amine, bis(imino) pyridine; 3,3'-iminodipropionitrile; [2,6-bis(1-phenylimino) ethyl]pyridine, norbornene diamide, methylene dianiline, hydrogenated methylene dianiline, durene diamine, 1,3-butadiene diepoxide, diepoxybutane, 1,6-diazacyclododecane-2,5-dione, dimethylbis(ureido)silane, ureidopyrimidinone tetrahydrophthalic anhydride, phthalic anhydride, isophthalic anhydride, hexahydrophthalic anhydride, maleic anhydride, succinic anhydride, dimethyl isophthalate, 1,4-cyclohexanedicarboxylic acid, dimethyl terephthalate, adipic acid, sebacic acid, fumaric acid, azelaic acid, toluene diisocyanate, isophorone diisocyanate, and hydrogenated dicyclohexyl methane diisocyanate.

6. The alkoxylated polymer of claim 1, wherein the alkoxylated polymer is selected from the group consisting of alkoxylated polyester, alkoxylated polyurethane, and alkoxylated polyurethane-urea.

7. The alkoxylated polymer of claim 1, wherein the alkoxylated polymer is:
   an alkoxylated polyester comprising:
   a) a polyalkylene glycol copolymer backbone selected from copolymers of polyethylene glycol, and polypropylene glycol;
   b) one or more diols or polyols; and
   c) one or more diacids or acid anhydrides, or mixtures thereof; or
   an alkoxylated polyurethane comprising:
   a) a polyalkylene glycol polymer or copolymer backbone selected from copolymers of polyethylene glycol, polypropylene glycol, and copolymers thereof;
   b) one or more diisocyanates; and
   c) one or more diols or polyols.

8. The alkoxylated polymer of claim 1, wherein the polyalkylene glycol component is a block copolymer having two blocks of polyethylene glycol and one block of polypropylene glycol in a tri-block structure.

9. The alkoxylated polymer of claim 1, wherein the polyalkylene glycol component is a block copolymer having two blocks of polypropylene glycol and one block of polyethylene glycol in a tri-block structure.

10. The alkoxylated polymer of claim 1, wherein the polyalkylene glycol component is a copolymer having random sequences of polyethylene glycol and polypropylene glycol.

11. The alkoxylated polymer of claim 1, wherein the polyalkylene glycol component is a copolymer having tapered sequences of polyethylene glycol and polypropylene glycol.

12. The alkoxylated polymer of claim 1, wherein one or more of the polyfunctional monomers and/or oligomers is a —COOH functionalized diol.

13. The alkoxylated polymer of claim 1 wherein, when the one or more polyfunctional monomers or oligomers are
    (a) one or more diol or polyol, and
    (b) one or more diisocyanates,
wherein the polyalkylene glycol polymer or copolymer and the one or more diol or polyol together comprise an equimolar amount of hydroxyl groups relative to the isocyanate groups in the one or more diisocyanates.

14. The alkoxylated polymer of claim 1 wherein the one or more polyfunctional monomers or oligomers do not contain isocyanate groups.

15. The alkoxylated polymer of claim 1, wherein the polyalkylene glycol component is a copolymer of polyethylene glycol and polypropylene glycol.

16. The alkoxylated polymer of claim 15, wherein the copolymer has at least one reactive terminal end that is a site for alkoxylation.

17. A primer, ink, or coating composition comprising the alkoxylated polymer of claim 1.

18. The primer, ink, or coating composition of claim 17, wherein the alkoxylated polymer is a dispersing agent or a low tack binder.

19. The primer, ink, or coating composition of claim 17, which is a gravure or flexographic primer, ink, or coating composition.

20. The primer, ink, or coating composition of claim 17, wherein the alkoxylated polymer is present in an amount from about 0.1 to about 25 wt %.

21. The primer, ink, or coating composition of claim 17, wherein the primer, ink, or coating composition exhibits an improvement in a property that is at least one of opacity, gloss, scratch resistance, and laydown, when compared to a primer, printing ink, or coating composition not including an alkoxylated polymer.

22. A method of forming an alkoxylated in one polymerization step, comprising:
    polymerizing, in one step, a backbone-forming polyalkylene glycol polymer or copolymer having one or more alkoxylated sites in non-reactive form and at least one reactive terminal end with one or more polyfunctional monomers or oligomers having two or more functional polar groups with an active hydrogen, or mixtures thereof, wherein the polyalkylene glycol component is selected from copolymers and terpolymers of polyethylene glycol, polypropylene glycol, and polybutylene glycol.

23. The method of forming an alkoxylated polymer of claim 22, wherein at least one reactive terminal end is a site for an alkoxylation.

24. The method of forming an alkoxylated polymer of claim 22, wherein the functional polar groups are independently selected from hydroxyl, carboxyl, anhydride, epoxy, thiol, amino, imino or isocyanate.

25. The method of forming an alkoxylated polymer of claim 22, wherein the functional polar group is hydroxyl; and/or wherein one or more of the polyfunctional monomers and/or oligomers is a —COOH functionalized diol; and/or wherein one or more of the polyfunctional monomers and/or oligomers is a diacid, an acid anhydride, and/or mixtures thereof; and/or wherein one or more of the polyfunctional monomers and/or oligomers is a diol; and/or wherein one or more of the polyfunctional monomers and/or oligomers are two or more diols.

26. The method of forming an alkoxylated polymer of claim 22, wherein the alkoxylated polymer is selected from alkoxylated polyester, alkoxylated polyurethane, and alkoxylated polyurethane-urea.

27. The method of forming an alkoxylated polymer of claim 22, wherein the alkoxylated polymer is:
    an alkoxylated polyester comprising:
        a) a polyalkylene glycol copolymer backbone selected from copolymers of polyethylene glycol, polypropylene glycol;
        b) one or more diols or polyols; and
        c) one or more diacids or acid anhydrides, or mixtures thereof;
or
    an alkoxylated polyurethane comprising:
        a) a polyalkylene glycol polymer or copolymer backbone selected from copolymers of polyethylene glycol, polypropylene glycol, and copolymers thereof;
        b) one or more diisocyanates; and
        c) one or more diols or polyols.

28. The method of claim 22 wherein, when the one or more polyfunctional monomers or oligomers are
    (a) one or more diol or polyol, and
    (b) one or more diisocyanates,
wherein the polyalkylene glycol polymer or copolymer and the one or more diol or polyol together comprise an equimolar amount of hydroxyl groups relative to the isocyanate groups in the one or more diisocyanates.

29. The method of claim 22 wherein the one or more polyfunctional monomers or oligomers do not contain isocyanate groups.

30. The method of forming an alkoxylated polymer of claim 22, wherein the polyalkylene glycol polymer or copolymer is a copolymer of polyethylene glycol and polypropylene glycol, having two blocks of polyethylene glycol and one block of polypropylene glycol in a tri-block structure, or having two blocks of polyethylene glycol and one block of polypropylene glycol in a tri-block structure, or random sequences of polyethylene glycol and polypropylene glycol, or tapered sequences of polyethylene glycol and polypropylene glycol.

31. The method of forming an alkoxylated polymer of claim 30, wherein the copolymer has at least one reactive terminal end that is a site for alkoxylation.

* * * * *